(12) United States Patent
Kusari et al.

(10) Patent No.: US 9,018,202 B2
(45) Date of Patent: Apr. 28, 2015

(54) METHODS FOR TREATING DISEASES OF THE RETINA

(75) Inventors: Jyotirmoy Kusari, Irvine, CA (US); Sheila X. Zhou, Irvine, CA (US); Mingting Tian, Irvine, CA (US); Edwin U. Padillo, Orange, CA (US); Sandhya S. Rao, Irvine, CA (US); Daniel W. Gil, Corona Del Mar, CA (US); Larry A. Wheeler, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/298,028

(22) Filed: Nov. 16, 2011

(65) Prior Publication Data

US 2012/0142675 A1 Jun. 7, 2012

Related U.S. Application Data

(60) Provisional application No. 61/419,660, filed on Dec. 3, 2010.

(51) Int. Cl.
*A61K 31/55* (2006.01)
*A61K 31/5513* (2006.01)

(52) U.S. Cl.
CPC .......... *A61K 31/5513* (2013.01); *Y10S 514/912* (2013.01)

(58) Field of Classification Search
USPC ................................................. 514/220, 912
See application file for complete search history.

(56) References Cited

U.S. PATENT DOCUMENTS

| | | | |
|---|---|---|---|
| 5,744,468 A * | 4/1998 | Lin et al. ........................ | 514/220 |
| 6,121,259 A * | 9/2000 | Yelle ............................. | 514/220 |
| 2003/0130266 A1 * | 7/2003 | Radulovacki et al. ........ | 514/220 |
| 2006/0210604 A1 | 9/2006 | Dadey et al. | |

FOREIGN PATENT DOCUMENTS

| | | |
|---|---|---|
| EP | 1478365 | 11/2004 |
| WO | WO 03070249 A1 * | 8/2003 |
| WO | 2004/103263 A2 | 12/2004 |
| WO | WO 2004103263 A2 * | 12/2004 |

OTHER PUBLICATIONS

Izzotti et al., The role of oxidative stress in glaucoma, Mutat Res. Mar. 2006;612(2), printed from http://www.ncbi.nlm.nih.gov/pubmed/16413223, abstract only, 2 pages.*
Gurler et al., The role of oxidative stress in diabetic retinopathy, Eye (Lond). Oct. 2000;14 Pt 5, printed from http://www.ncbi.nlm.nih.gov/pubmed/11116694, Abstract only, 2 pages.*
American Macular Degeneration Foundation , "Wet" Macular Degeneration, Feb. 4, 2005, printed from http://web.archive.org/web/20050204060925/http://www.macular.org/wet.html, 4 pages.*
Williams BK Jr, Schefler Ac, Murray TG . Eye tumors: an overview. Atlas Genet Cytogenet Oncol Haematol. Jul. 2010, 29 pages.*
Burstein et al., Intrinsic efficacy of antipsychotics at human D2, D3, and D4 dopamine receptors: identification of the clozapine metabolite N-desmethylclozapine as a D2/D3 partial agonist, J Pharmacol Exp Ther. Dec. 2005;315(3):1278-87. Epub Aug. 31, 2005.*
Jing Chen, et al., Erythropoietin deficiency decreases vascular stability in mice, Journal of Clinical Investigation, 2008, 118/2, 526-533.
Yanyan Bai, et al, Muller cell-derived VEGF is a significant contributor to retinal neovascularization, J Pathol, Aug. 11, 2009, 219, 446-454.
Louis E. H. Smith, et al., Oxygen-Induced Retinopathy in the Mouse, Investigative Ophthalmology, 1994, 35/1, 101-111.
International Search Report for PCT/US2011/061370, Feb. 29, 2012.
Barbel Rohrer et al., A Targeted Inhibitor of the Alternative Complement Pathway Reduces Angiogenesis in a Mouse Model of Age-Related Macular Degernation, Investigative Ophthalmology & Visual Science, Jul. 2009, 3056-3064, 50, No. 7, US.
Barbel Rohrer et al., Eliminating Complement Factor D Reduces Photoreceptor Susceptibility to Light-Induced Damage, Investigative Ophthalmology & Visual Science, Nov. 2007, 5282-5289, 48, No. 11, US.
C.J. Zeiss, Animals as Models of Age-Related Macular Degneration: An Imperfect Measure of the Truth, Veterinary Pathology Online, 2010, 396-413, 47-3, SAGE.
Dobi, Ernest T. et al., A New Model of Experimental Choroidal Neovascularization in the Rat, Arch Ophthalmol, Feb. 1989, 264-269, vol. 107.
Fernando Curz-Guilloty et al., The Pathogenesis of Dry Age-related Macular Degeneration: Lessons learned from animals, Retina Today, Apr. 2011, 71-75, US.
Iris Pharma, Retinal Degeneration: a new model of blue light-induced damage at Iris Pharma, Mar. 2010, www.iris-pharma.com/press-release/retinal-degeneration, 1 of 1 page, printed 0/16/13.
Robert E. Marc et al., Extreme retinal remodeling triggered by light damage: implications for age related macular degeneration, Molecular Vision 2008, 2008, 782-806, 14, US.
Robert J. Collier et al., Agonists at the Serotonin Receptor (5-HT1A) Protect the Retina from Severe Photo-Oxidative Stress, Investigative Ophthalmology & Visual Science, 2011, 2118-2126, No. 5, US.
Robert N. Frank et al., A model of subretinal neovascularization in the pigmented rat, Current Eye Research, 1989, 239-247, 8, No. 3.
Stephen J Ryan, M.D., Subretinal Neozascularization: Natural History of an Experimental Model, Arch Ophthalmol, Nov. 1982, 1804-1809, 100.
Stephen J. Ryan, M.D., The Development of an Experimental Model of Subretinal Neovascularization in Disciform Macular Degeneration, Trans Am Opthalmol Soc., 1979, 707-745, 77.
Wielgus, A.R. et al, Blue Light Induced A2E Oxidation in Rat Eyes—Experimental Animal Model of Dry AMD, Photochemical & Photobiological Sciences, 2010, 1505-1512, 9.

* cited by examiner

*Primary Examiner* — Gigi Huang
(74) *Attorney, Agent, or Firm* — Laura L. Wine; Joel B. German; Debra D. Condino

(57) ABSTRACT

Disclosed herein is a method of treating disorders of the retina comprising administering to a patient in need of such treatment a compound selected from the group consisting of olanzapine, certain of its metabolites, clozapine, and n-desmethyl clozapine.

4 Claims, 11 Drawing Sheets

METHODS FOR TREATING DISEASES OF THE RETINA

CROSS REFERENCE TO RELATED APPLICATIONS

This application claims the benefit of U.S. Provisional Application No. 61/419,660, filed Dec. 3, 2010, which is incorporated herein by reference in its entirety.

FIELD OF THE INVENTION

The present invention relates to methods of treating diseases affecting the retina by administering to a patient in need of such treatment clozapine, n-desmethyl clozapine, olanzapine, certain metabolites of olanzapine and various other compounds as set forth herein below.

SUMMARY OF THE INVENTION

The present invention discloses a method of treating a retinal disorder which is caused or aggravated by oxidative stress, the method comprising administering to a patient in need thereof a compound selected from the group consisting of

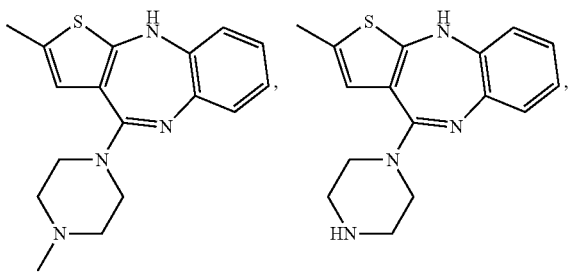

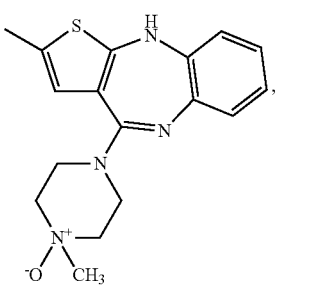

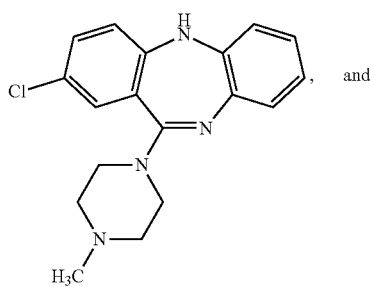

and

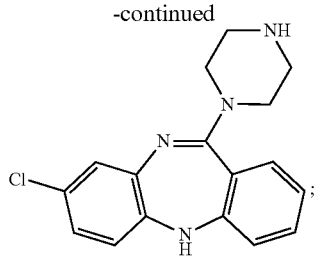

or a pharmaceutically acceptable salt thereof.

In another embodiment, the retinal disorder sought to be treated is selected from the group consisting of wet and dry age related macular degeneration, retinitis pigmentosa, Stargardt's disease cone dystrophy and pattern dystrophy of the retinal pigmented epithelium, macular edema, retinal detachment, retinal trauma, retinal tumors and retinal diseases associated with said tumors, congenital hypertrophy of the retinal pigmented epithelium, acute posterior multifocal placoid pigment epitheliopathy, and acute retinal pigment epithelitis. In another embodiment, the retinal disorder is selected from the group consisting of wet and dry age related ma1cular degeneration retinitis pigmentosa, Stargardt's disease cone dystrophy and pattern dystrophy of the retinal pigmented epithelium, congenital hypertrophy of the retinal pigmented epithelium, acute posterior multifocal placoid pigment epitheliopathy, and acute retinal pigment epithelitis.

In another embodiment, the compound that is administered is administered orally.

In another embodiment, the compound that is administered is administered by injecting it into the eye.

In another embodiment, the compound that is administered is administered topically to the eye.

DETAILED DESCRIPTION OF THE INVENTION

Conditions of the Retina

Figure 1:
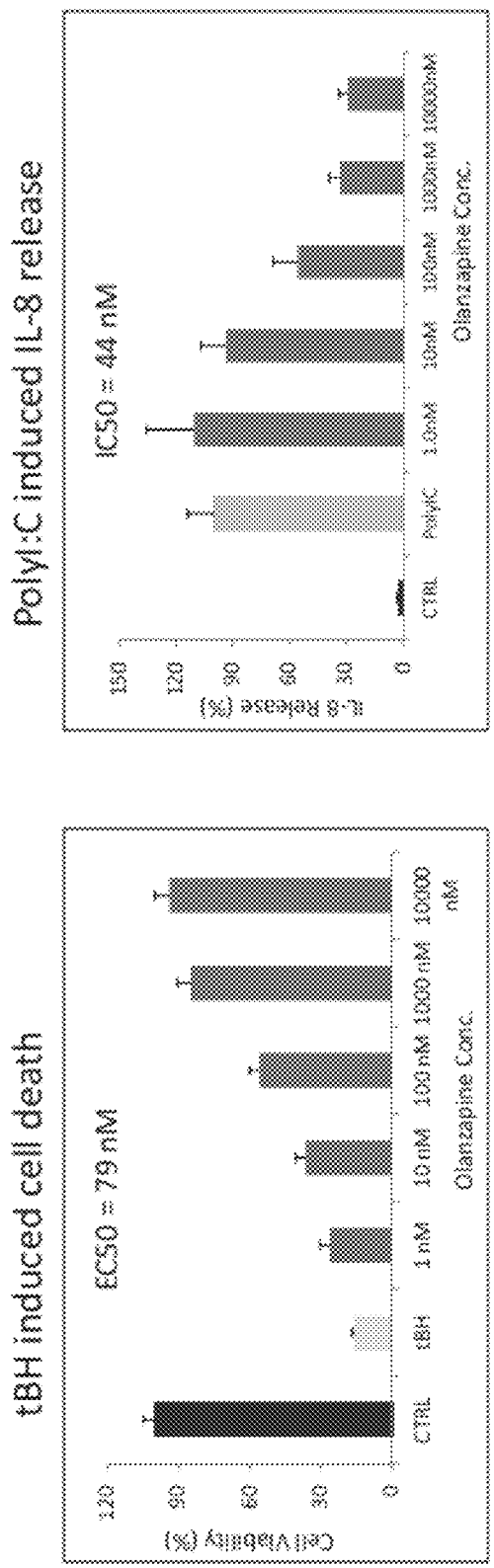
FIG. 1 shows that olanzapine significantly protects in a dose responsive fashion retinal pigmented epithelium (RPE) cells from oxidative stress (tBH) induced apoptosis (A) & inhibits Poly I:C induced IL-8 secretion from RPE cells (B). Error bars, SEM.

The compound of the invention may be used to treat diseases of the retina. By "diseases of the retina," the applicants mean any condition of the retina or the tissues that surround it which are caused or aggravated by oxidative stress. These include macular degeneration, diabetic retinopathy, choroidal neovascular membrane, macular edema (also referred to as cystoid macular edema and macular swelling), epiretinal membrane (macular pucker), macular hole, retinitis pigmentosa, macular dystrophies (such as Stargardt's juvenile macular degeneration, Best's vitelliform dystrophy, cone dystrophies, and pattern dystrophy of the retinal pigmented epithelium), retinal detachment, retinal trauma, retinal tumors and retinal diseases associated with them, congenital hypertrophy of the retinal pigmented epithelium, acute posterior multifocal placoid pigment epitheliopathy, and acute retinal pigment epithelitis.

Macular degeneration, also referred to as age-related macular degeneration, is the most common cause of vision loss in the United States in those 50 or older, and its prevalence increases with age. AMD is classified as either wet (neovascular) or dry (non-neovascular). The dry form of the disease is most common. It occurs when the central retina has become distorted, pigmented, or most commonly, thinned, a process associated with atrophy of the retinal pigment epithelium and loss of macular photoreceptors. The result is central geographic atrophy. The wet form of the disease is responsible for most severe loss of vision. The wet form is usually associated with aging, but other diseases that can cause wet macular degeneration include severe myopia and some intraocular infections such as histoplasmosis, which may be exacerbated in individuals with AIDS. The wet form is characterized by abnormal blood vessels growing through the retinal pigment epithelium, resulting in hemorrhage, exudation, scarring, or retinal detachment.

Retinopathy associated with diabetes is a leading cause of blindness in type 1 diabetes, and is also common in type 2 diabetes. The degree of retinopathy depends on the duration of the diabetes, and generally begins to occur ten or more years after onset of diabetes. Diabetic retinopathy may be classified as (1) non-proliferative or background retinopathy, characterized by increased capillary permeability, edema, hemorrhage, microaneurysms, and exudates; or 2) proliferative retinopathy, characterized by neovascularization extending from the retina to the vitreous, scarring, fibrous tissue formation, and potential for retinal detachment. Diabetic retinopathy is believed to be caused, at least in part, by the development of glycosylated proteins due to high blood glucose. Glycosylated proteins generate free radicals, resulting in oxidative tissue damage and depletion of cellular reactive oxygen species (ROS) scavengers, such as glutathione.

In choroidal neovascular membrane, abnormal blood vessels stemming from the choroid grow up through the retinal layers. The fragile new vessels break easily, causing blood and fluid to pool within the layers of the retina.

In macular edema, which can occur as a result of disease, injury or surgery, fluid collects within the layers of the macula, causing blurred, distorted central vision.

Epiretinal membrane is a cellophane-like membrane that forms over the macula, affecting the central vision by causing blur and distortion. As it progresses, the traction of the membrane on the macula may cause swelling. The disease is seen most often in people over 75 years of age.

Retinitis pigmentosa is a retinal degeneration characterized by night blindness and progressive loss of peripheral vision, eventually leading to total blindness; ophthalmoscopic changes include dark mosaic-like retinal pigmentation, attenuation of the retinal vessels, waxy pallor of the optic disc, and in the advanced forms, macular degeneration. In some cases there can be a lack of pigmentation Retinitis pigmentosa can be associated to degenerative opacity of the vitreous body, and cataract.

Macular dystrophy is a term applied to a heterogeneous group of diseases that collectively are the cause of severe visual loss in a large number of people. A common characteristic of macular dystrophy is a progressive loss of central vision resulting from the degeneration of photoreceptor cells in the retinal macula. In many forms of macular dystrophy, the end stage of the disease results in legal blindness. More than 20 types of macular dystrophy are known. Some of these are, for example, age-related macular dystrophy, Stargardt-like dominant macular dystrophy, recessive Stargardt's disease, atypical vitelliform macular dystrophy (VMD1), Usher Syndrome Type 1B, autosomal dominant neovascular inflammatory vitreoretinopathy, familial exudative vitreoretinopathy, and Best's macular dystrophy (also known as hereditary macular dystrophy or Best's vitelliform macular dystrophy (VMD2).

Stargardt-like dominant macular dystrophy (also called autosomal dominant macular atrophy) is a juvenile-onset macular degeneration. Patients afflicted with this disease generally have normal vision as young children, but during childhood, visual loss begins, which rapidly progresses to legal blindness. Clinically it is characterized by the presence of an atrophic macular lesion with sharp borders and is often associated with yellow fundus flecks.

Best's macular dystrophy is an inherited autosomal dominant macular dystrophy of unknown biochemical cause. The disease has an age of onset that can range from childhood to after 40. Clinical symptoms include, at early stages, an abnormal accumulation of the yellowish material lipofuscin in the retinal pigmented epithelium (RPE) underlying the macula. This gives rise to a characteristic "egg yolk" appearance of the RPE and gradual loss of visual acuity. With increasing age, the RPE becomes more and more disorganized, as the lipofuscin accumulations disperse and scarring and neovascularization take place. These changes are accompanied by further loss of vision.

The pathological features seen in Stargardt-like dominant macular dystrophy and Best's macular dystrophy are in many ways similar to the features seen in age-related macular dystrophy (AMD), the leading cause of blindness in older patients in the developed world.

Retinal detachment occurs when the sensory layers of the retina become separated from their underlying supporting tissue of retinal pigment epithelium and the choroid. Generally, retinal detachment is caused by a retinal tear or the presence of vitreous traction, either of which may occur spontaneously or may be due to trauma. Retinal detachment may also result from pathology, such as retinopathy of prematurity in premature infants or diabetic retinopathy in diabetic individuals. Symptoms of retinal detachment are painless and sudden segmental or total visual loss in one eye. When there is a tear, or when there is traction causing separation of the retina from its underlying structures, the liquid vitreous passes through the opening and into the subretinal space, inducing further exudation in the subretinal space. The retina gradually separates and detaches from the underlying retinal pigment epithelium. This deprives the outer retina of its normal supply of oxygen and nutrients from the choroid. With time, retinal detachment also results in loss of vision, due to loss of photoreceptor cells located in the outer part of the retina.

By "treat," the applicants mean to deal with medically. The term includes administering the compound of the invention to alleviate symptoms of a retinal disease, such as the decrease in visual acuity that accompanies macular degeneration, as well as to address the physiological changes associated with the disease, such as the abnormal blood vessel growth that accompanies that condition.

Compounds of the Invention

Methods of the inventions treat retinal disease by administering to a patient in need of such treatment clozapine, olanzapine, or certain metabolites of olanzapine. The compounds are well known.

Clozapine has been prescribed since the 1970s as an antipsychotic. It has the following structure:

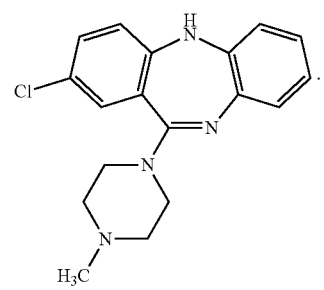 [SMILES: CN1CCN(C2=Nc3ccccc3Nc3ccc(Cl)cc32)CC1]

Its chemical name is 2-chloro-11-(4-methylpiperazin-1-yl)-5H-dibenzo[b,e][1,4]diazepine. It may be synthesized in various ways. One way is as follows:

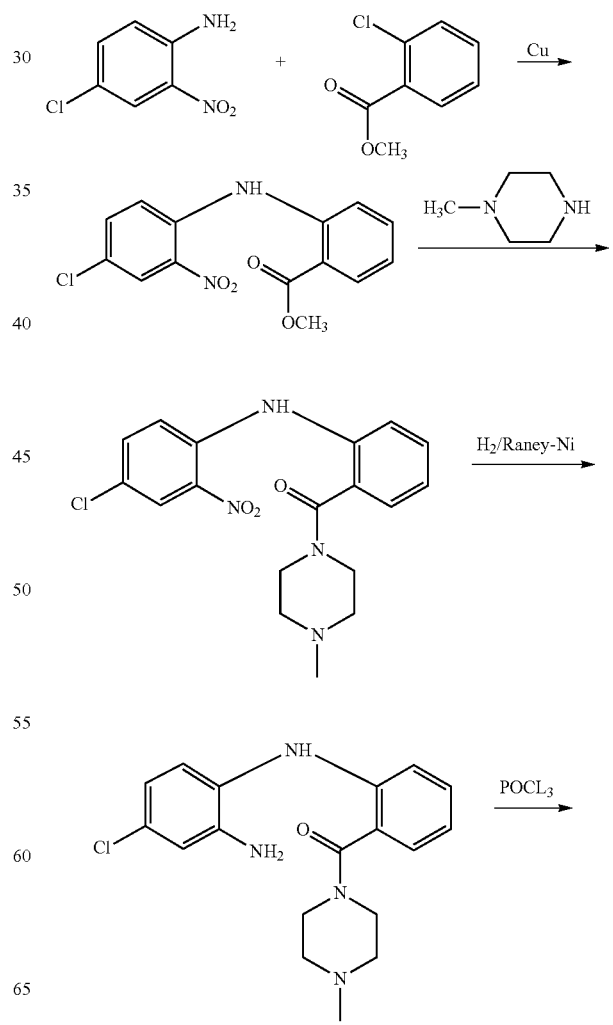

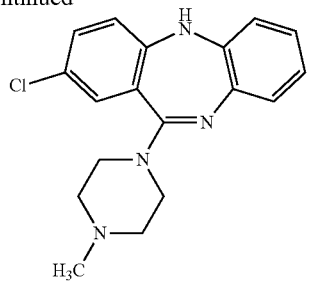

N-desmethyl clozapine, which has the structure

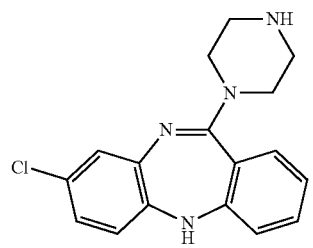 [SMILES: Clc1ccc2c(c1)N=C(N1CCNCC1)c1ccccc1N2]

Another way is as follows:

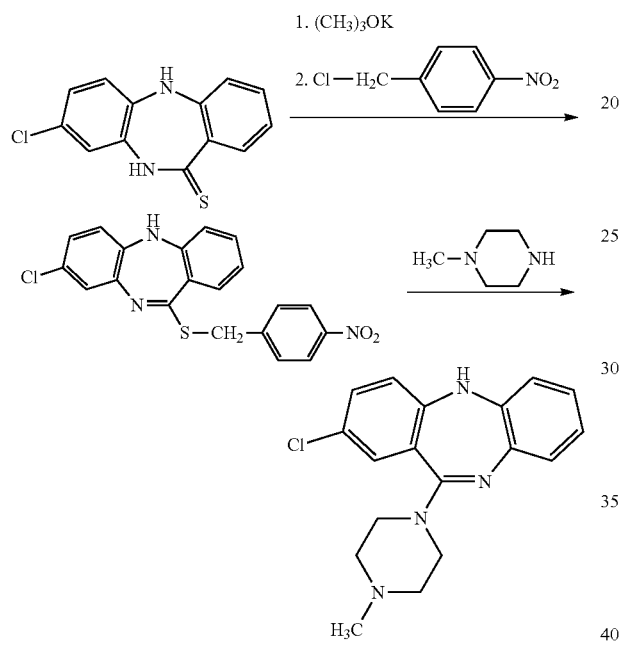

can be obtained from Tocris.

Olanzapine is another well known antipsychotic drug. It has the following structure:

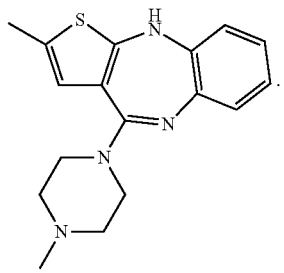 [SMILES: Cc1cc2c(s1)Nc1ccccc1N=C2N1CCN(C)CC1]

Its chemical name is 2-methyl-4-(4-methylpiperazin-1-yl)-10H-benzo[b]thieno[2,3-e][1,4]diazepine. Elli Lilly and Company markets the drug under the trade name Zyprexa. One way of making olanzapine is as follows. It is disclosed in U.S. Pat. No. 5,631,250, the contents of which are incorporated herein by reference:

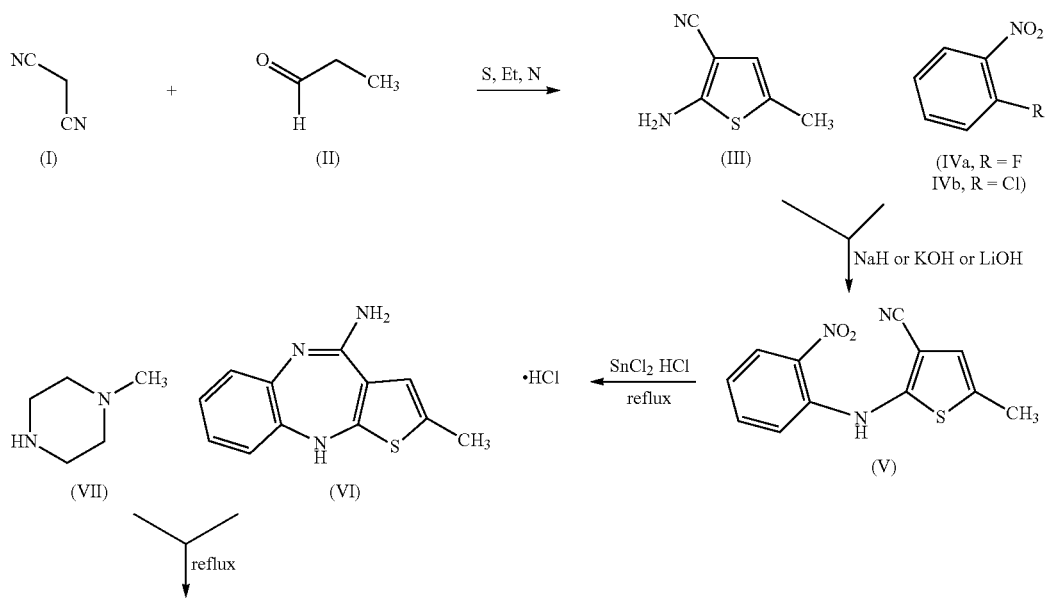

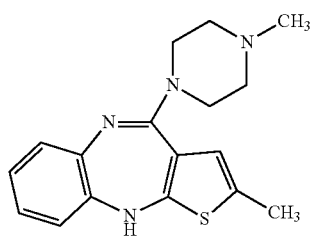

Another way is as follows. It is disclosed in U.S. Patent Application Publication No. 2006/035887, the contents of which are incorporated herein by reference:

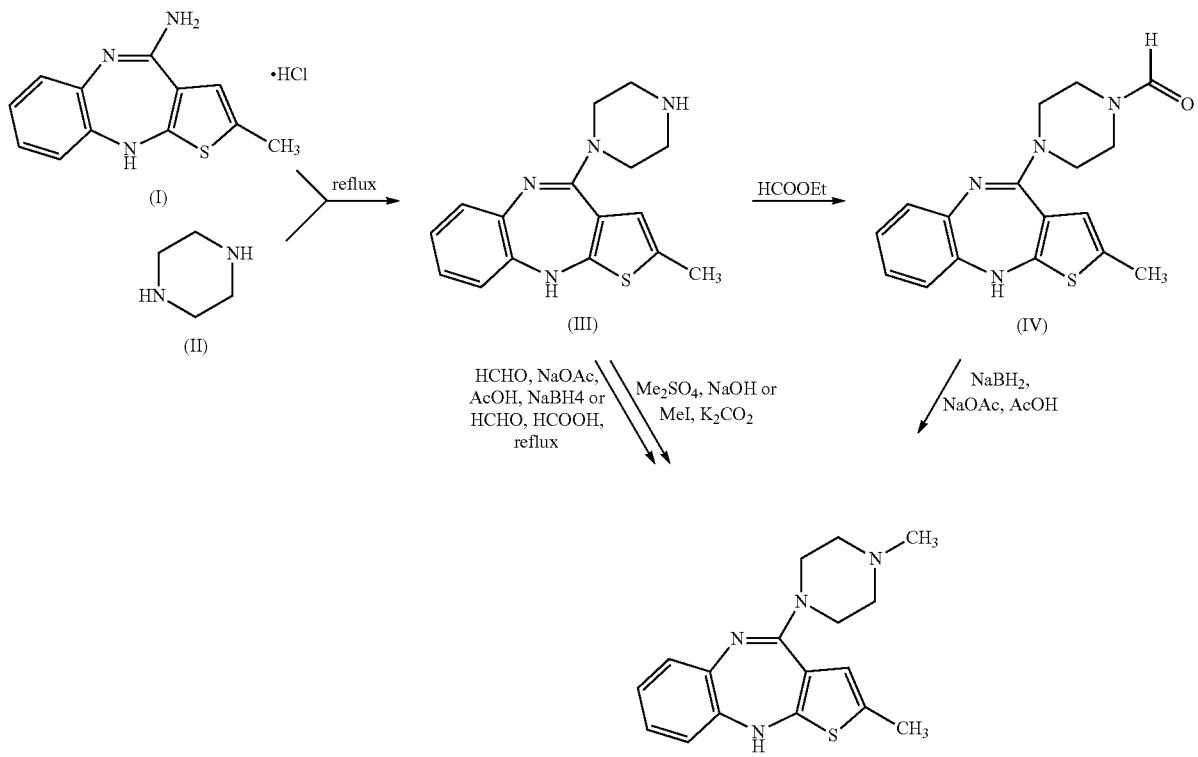

Olanzapine is metabolized to the following compounds, both of which may also be used in the method of the invention:

Metabolite A

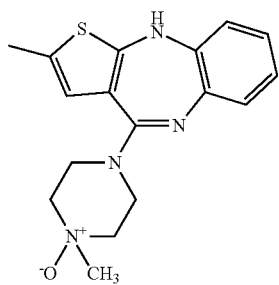

Metabolite B

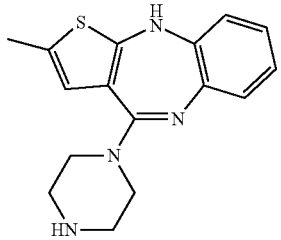

Olanzapine-N-oxide (Metabolite A) and N-demethyl olanzapine (Metabolite B) can be obtained from Toronto Research Chemical.

In one embodiment, one administers the compounds of the invention as pharmaceutically acceptable salts. A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di-, and tri-alkyl amines or ethanol amines. For a review on suitable salts, see Handbook of Pharmaceutical Salts: Properties, Selection, and Use by Stahl and Wermuth (Wiley-VCH, 2002).

Formulation and Administration

The compound of the invention may be administered via either the oral, transdermal (e.g. through the use of a patch), intranasal, sublingual, rectal, or parenteral routes. In one preferred embodiment, the compound is delivered by injecting it into the eye.

In one embodiment the compound is administered at doses ranging from about 0.25 mg up to about 1500 mg per day; in another embodiment the compound is administered at doses of 0.25 to about 300 mg per day in single or divided doses; in another embodiment the compound is administered at doses of 0.01 mg to about 10 mg per kg of body weight per day, although variations will necessarily occur depending upon the weight and condition of the subject being treated and the particular route of administration chosen, as well as the individual's responses to the treatment, the formulation chosen, and the length of time the patient is treated. In some instances, doses less than 0.25 mg per day may be adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, solutions, suspensions, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

In one embodiment of the invention, clozapine may be delivered topically to the eye or by injection into the eye. Suitable formulations for this purpose include liquids, suspensions, emulsions, and the like. Topical formulations of ophthalmic drug products are well known in the art and described in, for example, U.S. Patent Application Publication No. 20050059583; No. 20050277584; No. 20070015690; and No. 20070015691; and U.S. Pat. Nos. 5,474,979 and 6,582,718, the disclosures of all which are incorporated herein by reference.

In one embodiment, the clozapine formulation is administered as an eye drop; in a typical administration, 25 to 50 µl of the formulation is administered to the eye. Such formulations may be administered once, twice, three times, four times, or more, daily.

EXAMPLES

The invention is illustrated by the following examples.

ARPE-19 cells from ATCC were grown in DEME/F12 medium supplemented with 10% Fetal Bovine Serum (FBS) and split into 96-well plates at a density of 10,000 cells per well. Cells were incubated overnight in 0.1% FBS medium before addition of compound/drug. Stocks of compounds of interest were made at different concentrations and added to ARPE-19 cells in 0.1% FBS medium for one hour.

Figure 2:
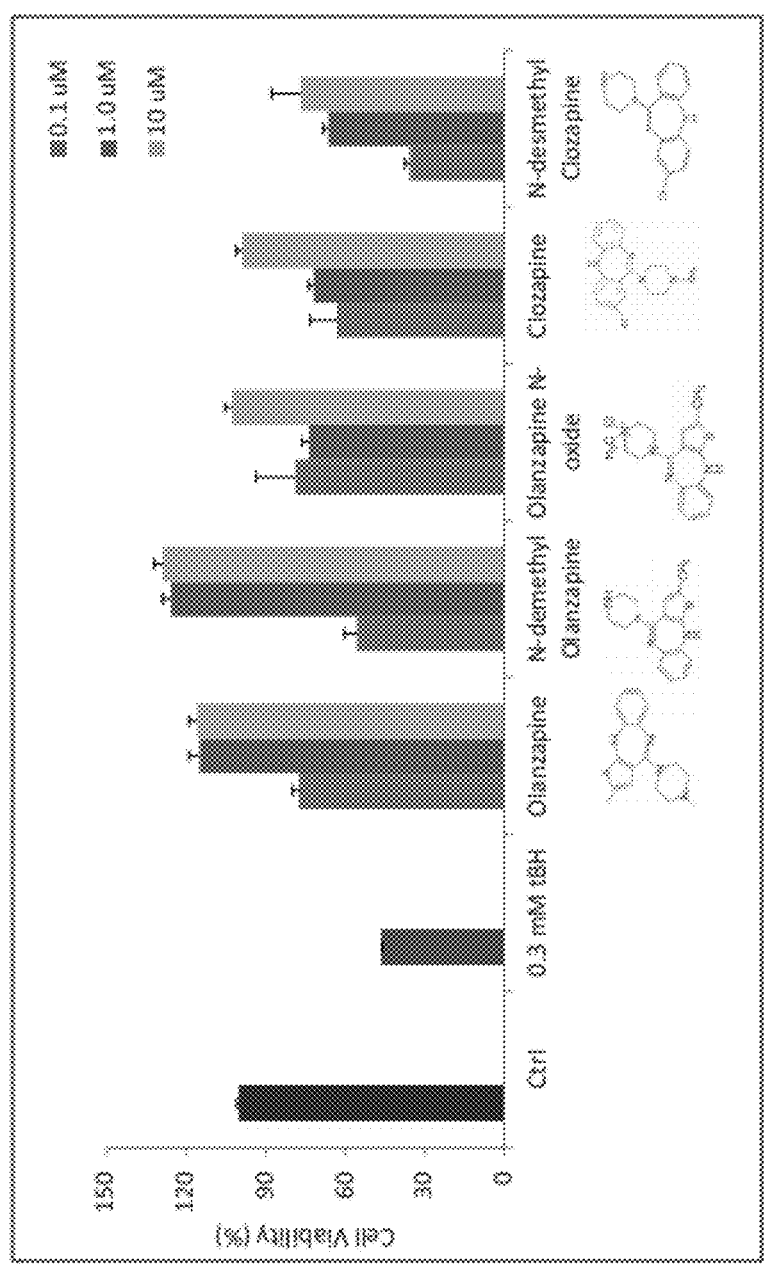
FIG. 2 shows that olanzapine, its metabolites, and clozapine protect RPEs from tBH induced cell death. Error bars, SEM.

Cell Viability Assay: After one hour of compound/drug pretreatment, cells were incubated with 0.3 mM tert-butyl hydroperoxide (tBH) for 3 hours followed by three times of washing and replacement with fresh drug and medium (0.1% FBS medium) for overnight. Cell viability was determined by cell proliferation assay kit (Millipore, 2210). Error bars, SEM. n=3. The results are shown in FIGS. 1, 2 & 12.

IL-8 Assay: After one hour of drug pretreatment, cells were incubated with 1 ug/ml polyI:C for 24 hours. The cell culture supernatant was used to measure IL-8 production with IL-8 ELISA Kit (R&D Systems, D8000C). Error bars, SEM. n=3. The results are shown in FIG. 1.

Blue Light Study: Four to five month old Sprague-Dawley (SD) male rats were used in the following study. Drug treatment was started 2 days before blue light exposure. Animals received olanzapine IP injection once per day for 3 days and the last dosing was 1 hour before blue light exposure.

Figure 3:
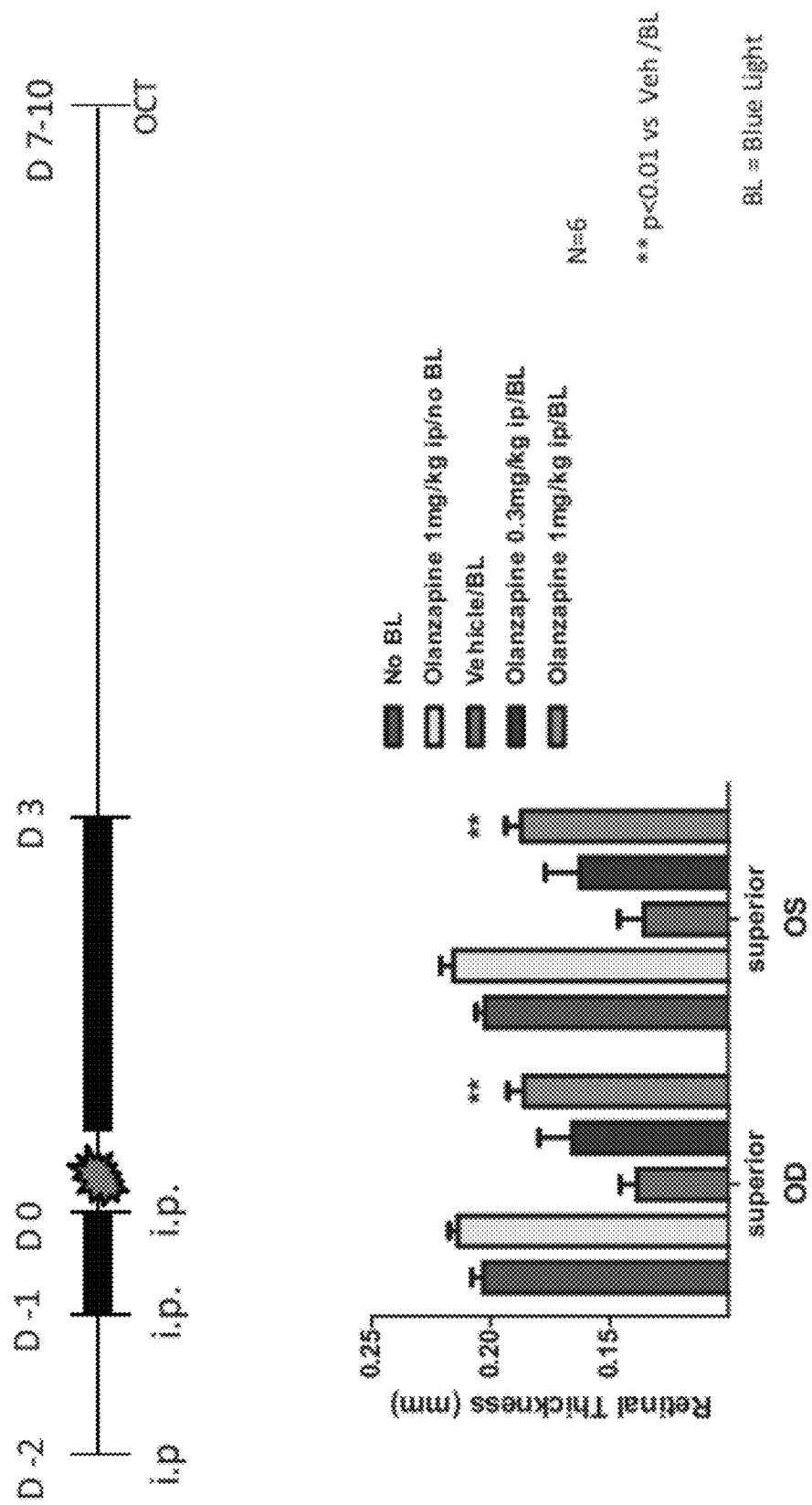
FIG. 3 shows that olanzapine significantly protects superior retinal thickness of blue light exposed rats. Drug treatment was started 2 days before blue light exposure. Animals received olanzapine IP injection once per day for 3 days and the last dosing was 1 hour before blue light exposure. Rats were dark adapted for 24 hours before they were exposed to blue light with lux intensity of ~6-7 k for 4 hours. Right after the blue light exposure, the rats were dark adapted again for another 3 days before returning to normal room light (12-hour light/12-hour dark). Optical coherence tomography (OCT) was used to evaluate the retinal thickness change caused by blue light at 7-10 days post blue light exposure. Error bars, SEM. OS=Left Eye, OD=Right Eye.

For intravitreal injection (IVT), animals received olanzapine (having the structure shown below) 1 hour before blue light exposure. For topical administration, the drug was given 24 hours (BID) and one hour (QI) before blue light exposure. Water was used for parallel control vehicle IP/IVT injection or topical administration. Rats were dark adapted for 24 hours before they were exposed to blue light with lux intensity of ~6-7 k for 4 hours. Right after the blue light exposure, the rats were dark adapted again for another 3 days before returning to normal room light (12-hour light/12-hour dark). Optical coherence tomography (OCT) was used to evaluate the retinal thickness change caused by blue light at 7-10 days post blue light exposure. Error bars, SEM. (FIG. 3).

Figure 4:
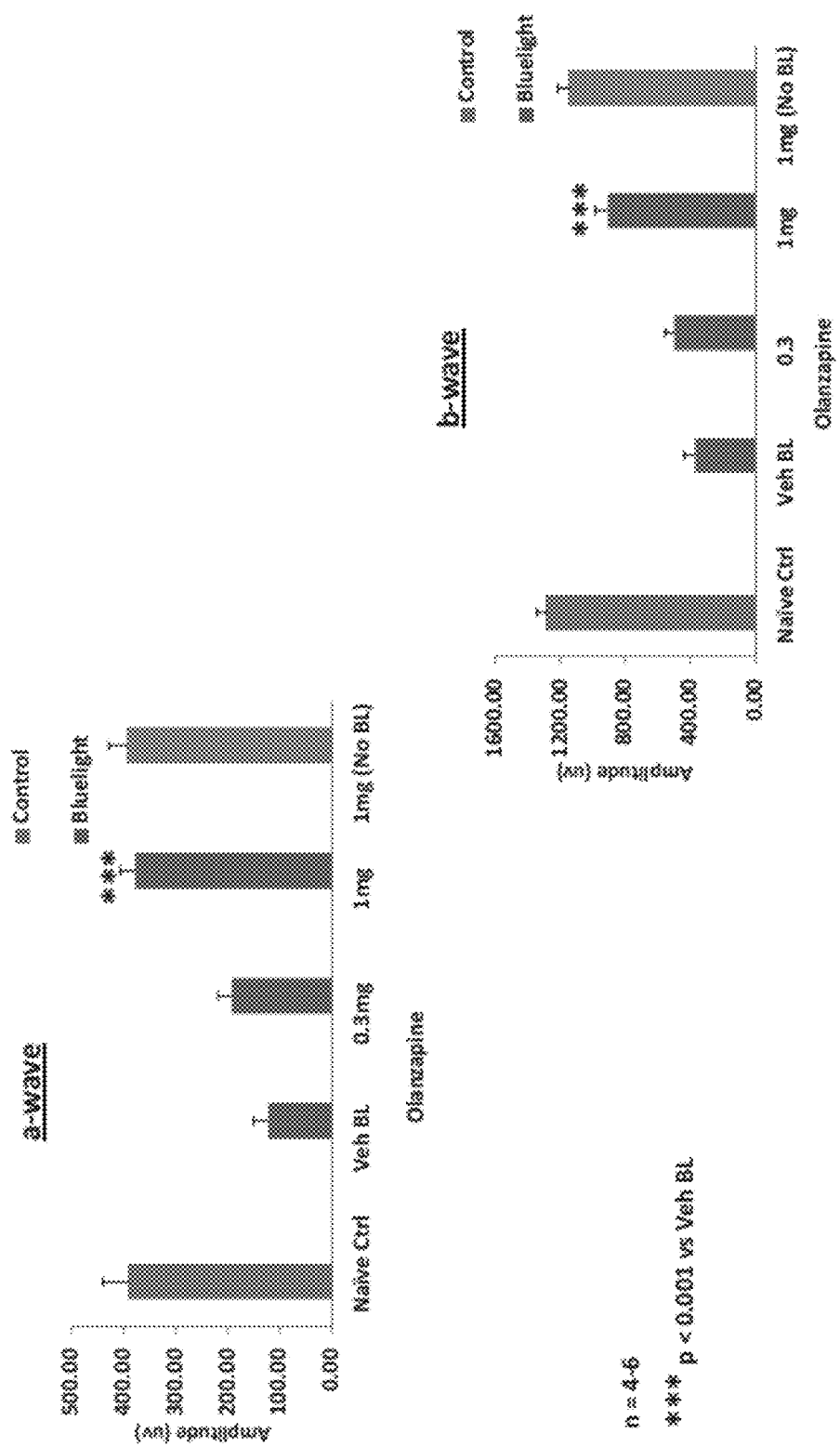
FIG. 4 shows that olanzapine significantly protects retinal a- and b-waves of blue light exposed rats. Drug treatment and dark adaptation were similar as described in FIG. 3. Electroretinograms were recorded at 7-10 days post blue light exposure. Error bars, SEM. BL=Blue Light.
Figure 8:
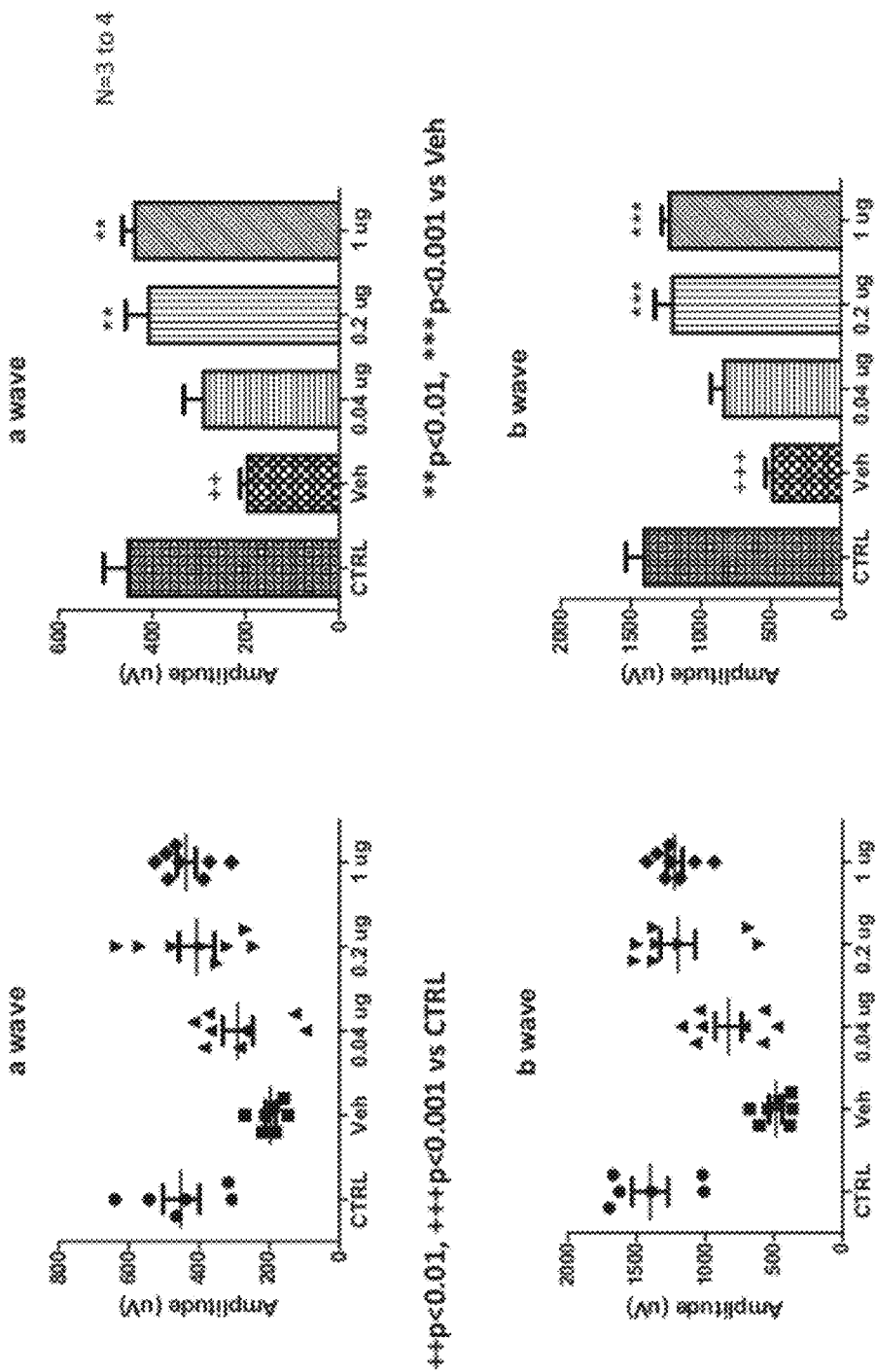
FIG. 8 shows that intravitreal delivery of olanzapine significantly prevents ERG alteration of blue light exposed rats. For intravitreal injection (IVT), animals received olanzapine 1 hour before blue light exposure. Water was used as a parallel control vehicle during IVT injection. Rats were dark adapted for 24 hours before they were exposed to blue light with lux intensity of ~6-7 k for 4 hours. Right after the blue light exposure, the rats were dark adapted again for another 3 days before returning to normal room light (12-hour light/12-hour dark). CTRL=Naïve Control, Veh=Water, 0.04, 0.2, or 1 ug of olanzapine/eye. Left Panel=Scattered plots of data from each eye and Right panel=Bar diagrams of average results. Electroretinograms were recorded at 7-10 days post blue light exposure. Error bars, SEM.
Figure 9:
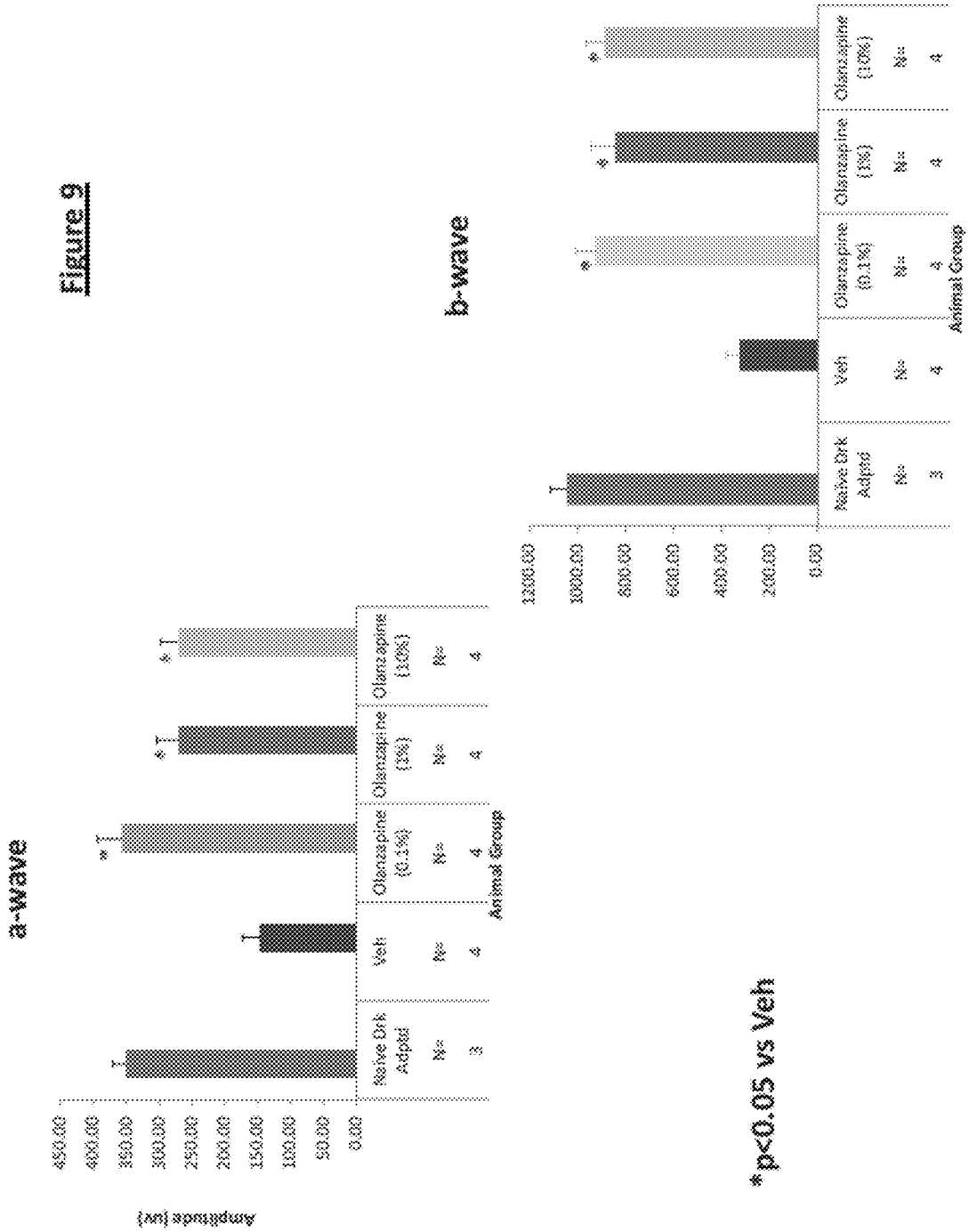
FIG. 9 shows that topical ocular dosing of olanzapine significantly protects retinal a- and b-wave signals of blue light exposed SD rats. For topical administration, the drug was given 24 hours (BID) and one hour (QI) before blue light exposure. Water was used as a parallel control vehicle during topical administration. Rats were dark adapted for 24 hours before they were exposed to blue light with lux intensity of ~6-7 k for 4 hours. Right after the blue light exposure, the rats were dark adapted again for another 3 days before returning to normal room light (12-hour light/12-hour dark). Electroretinograms were recorded at 7-10 days post blue light exposure. Error bars, SEM.

Electroretinography (ERG) Assay: Bilateral Flash Electroretinograms were recorded in SD rats using the Espion $E^2$ electroretinography system. On the day of ERG, Animals were dark adapted for at least 30 minutes. Their eyes were dilated with Tropicamide HCl (1%) and Ak-dilate (10%). Prior to ERG recording, the animal was anesthetized with intramuscular injection of 40 mg/ml Ketamine HCL and 12 mg/ml Xylazine HCL, and placed onto heated platform. The ground needle was placed in the skin under the arm and the reference needle was place in the skin above the head. Retinae were stimulated using 1 cd.s/m2 flash for an average of 10 traces at 0.1 Hz. Recording filter was set at 300 Hz. ERG responses were analyzed using Espion $E^2$, and Microsoft excel program. The b-wave amplitude was measured from the trough of the a-wave to the peak of the b-wave, and the a-wave was measured as the difference in amplitude between recording at onset and the trough of the negative deflection. Error bars, SEM. (FIGS. 4, 8, and 9)

Figure 5:
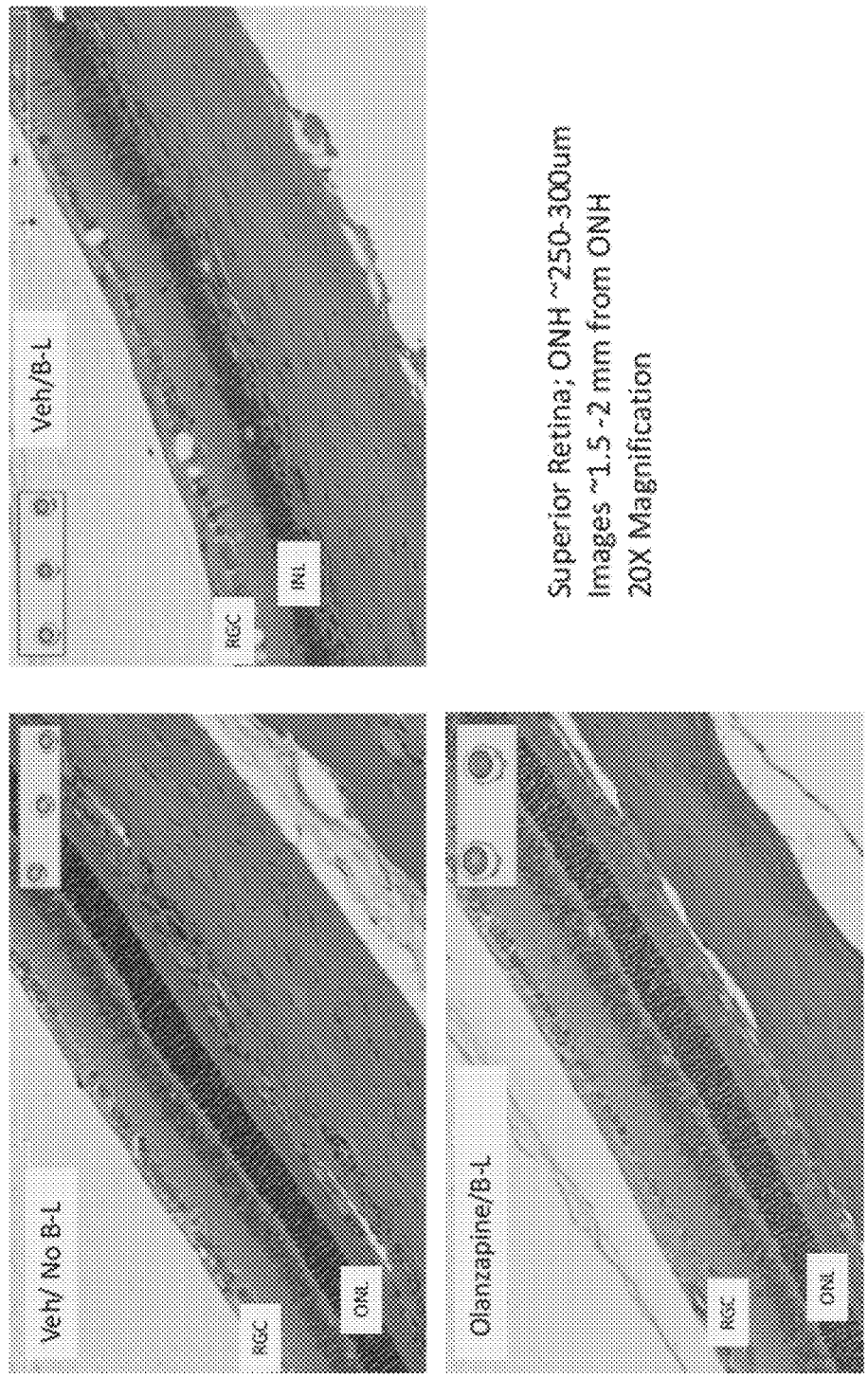
FIG. 5 shows that olanzapine significantly protects outer nuclear layer of blue light exposed rats. Drug treatment and dark adaptation were similar as described in FIG. 3. H&E staining was performed 2-3 wks after blue light exposure. B-L=Blue Light. ONH=Optic nerve head.
Figure 6:
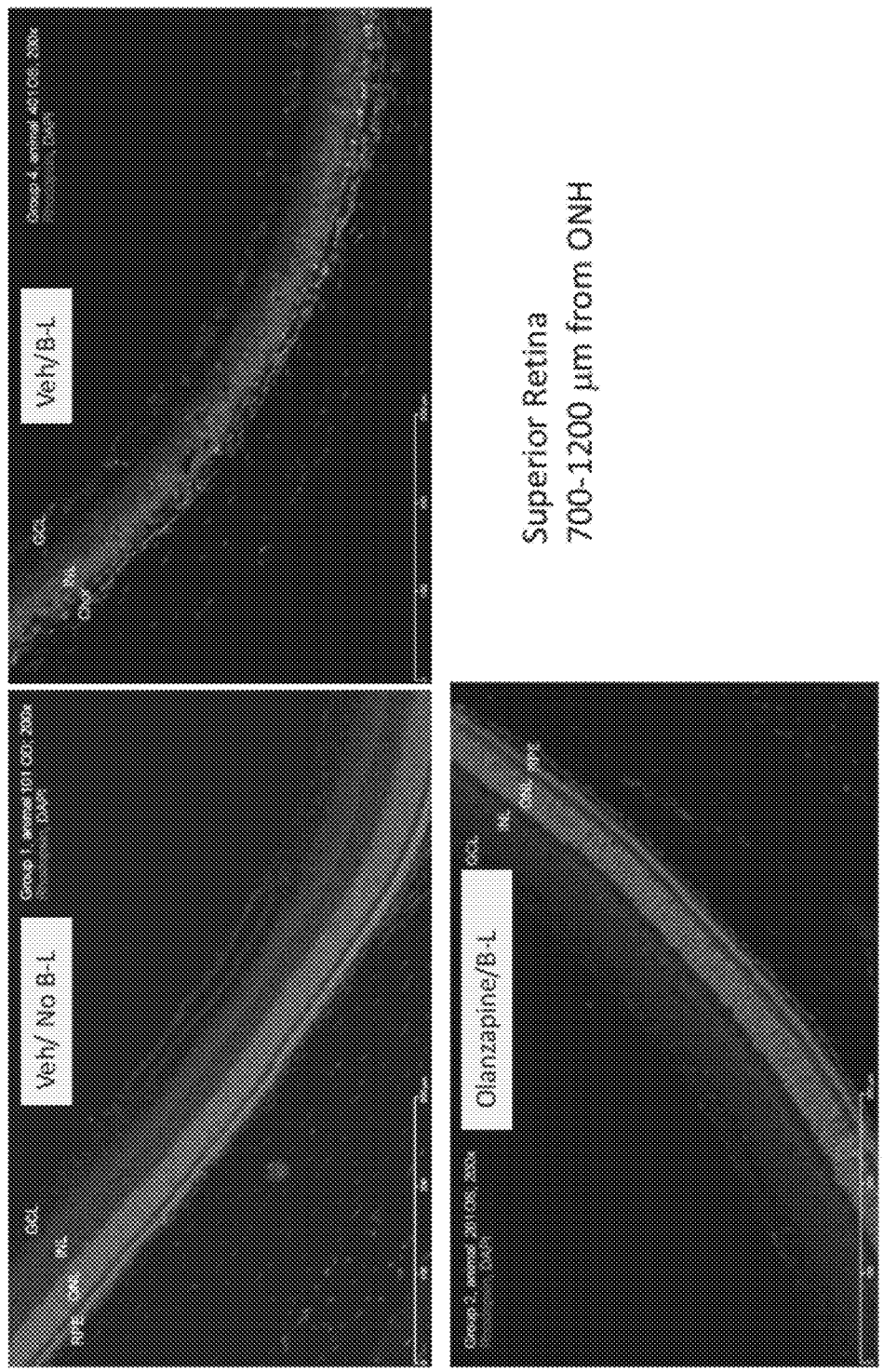
FIG. 6 shows that olanzapine significantly protects retinal rhodopsin loss caused by blue light exposure. Drug treatment and dark adaptation were similar as described in FIG. 3. Immuno-histochemistry study was performed 2-3 wks after blue light exposure. B-L=Blue Light. ONH=Optic nerve head.
Figure 7:
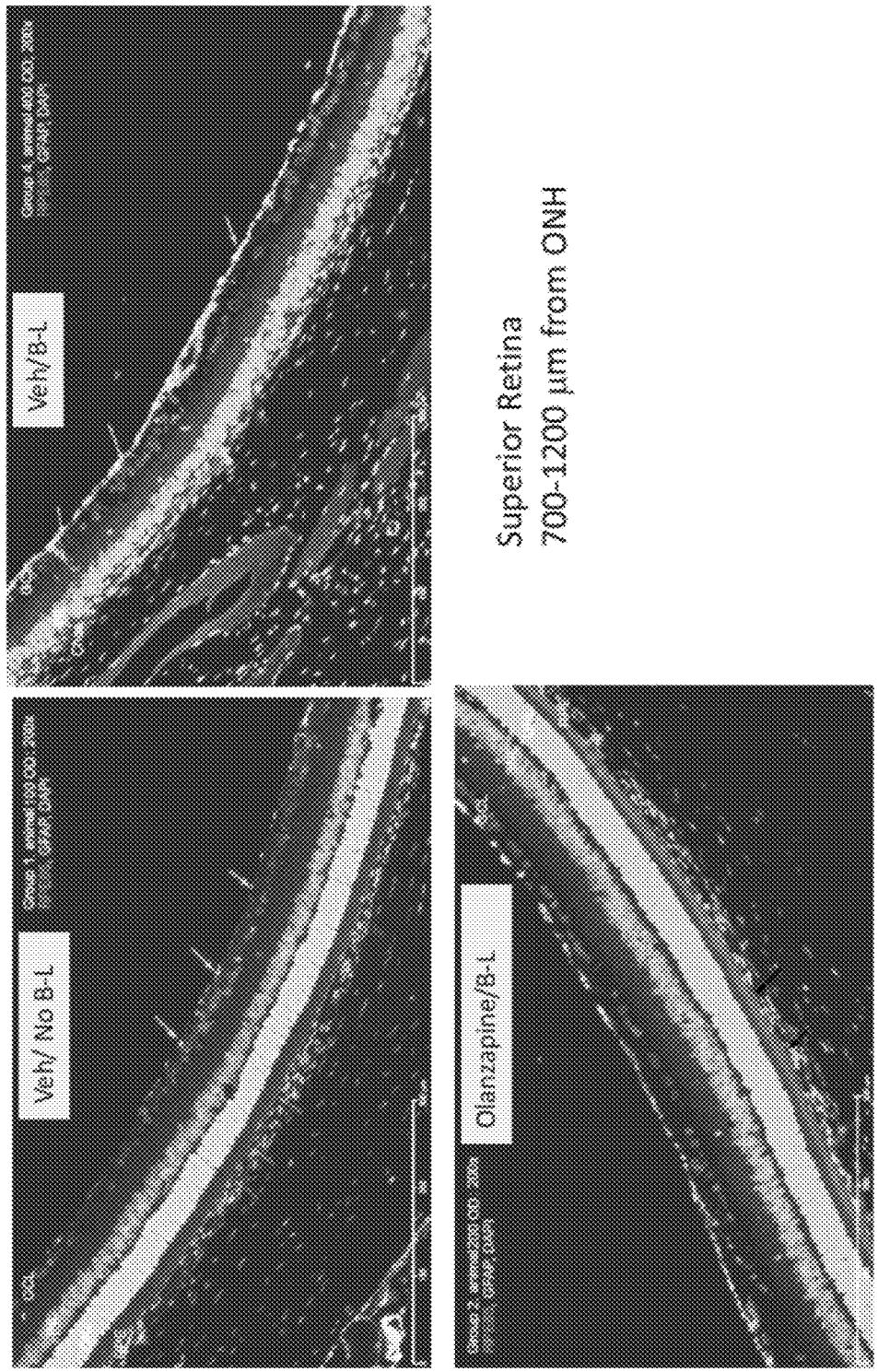
FIG. 7 shows that olanzapine significantly protects RPE65 loss and partially inhibits GFAP upregulation. Drug treatment and dark adaptation were similar as described in FIG. 3. Immuno-histochemistry study was performed 2-3 wks after blue light exposure. B-L=Blue Light. ONH=Optic nerve head.

Rat Ocular Tissue Processing & H&E staining: Sprague-Dawley male rats 2-3 weeks after blue light exposure were euthanized with $CO_2$ and orbits enucleated. Eyes were fixed in Davidson's fixative overnight at room temperature and transferred to 70% ethanol for 24 hrs. Further tissue processing was done by serial dehydration in 80%, 95% & 100% alcohol and Propar, followed by paraffin embedding. Whole rat eyes were transversely cut in the vertical meridian proceeding from nasal to temporal side, using a Microtome (RM2255; Leica Microsystems). Using optic nerve head as the landmark, a total of 45 serial sections with 5 microns/section were collected on 15 glass slides. Slide #s 1,5,10 & 15 were diparaffinized and sequentially stained using hematoxylin (nucleus) and eosin (cytoplasm) as per standard protocol to compare photoreceptor/RPE lesion between experimental groups. The rest of the slides were used to determine expressions of Rhodopsin, RPE65 and GFAP using the specific antibodies by standard immune-histochemistry techniques. The results are shown in FIGS. 5-7.

Oxygen-induced retinopathy: Oxygen-induced retinopathy (OIR)/Hyperoxia was induced in C57B6 mice using the protocol reported by Smith et al. (Smith L E, Wesolowski E, McLellan A, et al. Oxygen-induced retinopathy in the mouse. *Invest Ophthalmol Vis Sci.* 1994;35(1):101-111). Litters of newborn mice and their dams were placed in a 75% oxygen chamber from P7 to P12. The chamber contained enough food and water for 5 days and was opened only to allow drug administration to the animals. The mice were returned to room air with normal oxygen content on P12. Olanzapine in water or VEH (water) was administered once daily by gavage beginning on P10 and continuing through P16. Retinal neovascularization was evaluated on P17 after 5 days of exposure of the animals to room air.

Figure 10:
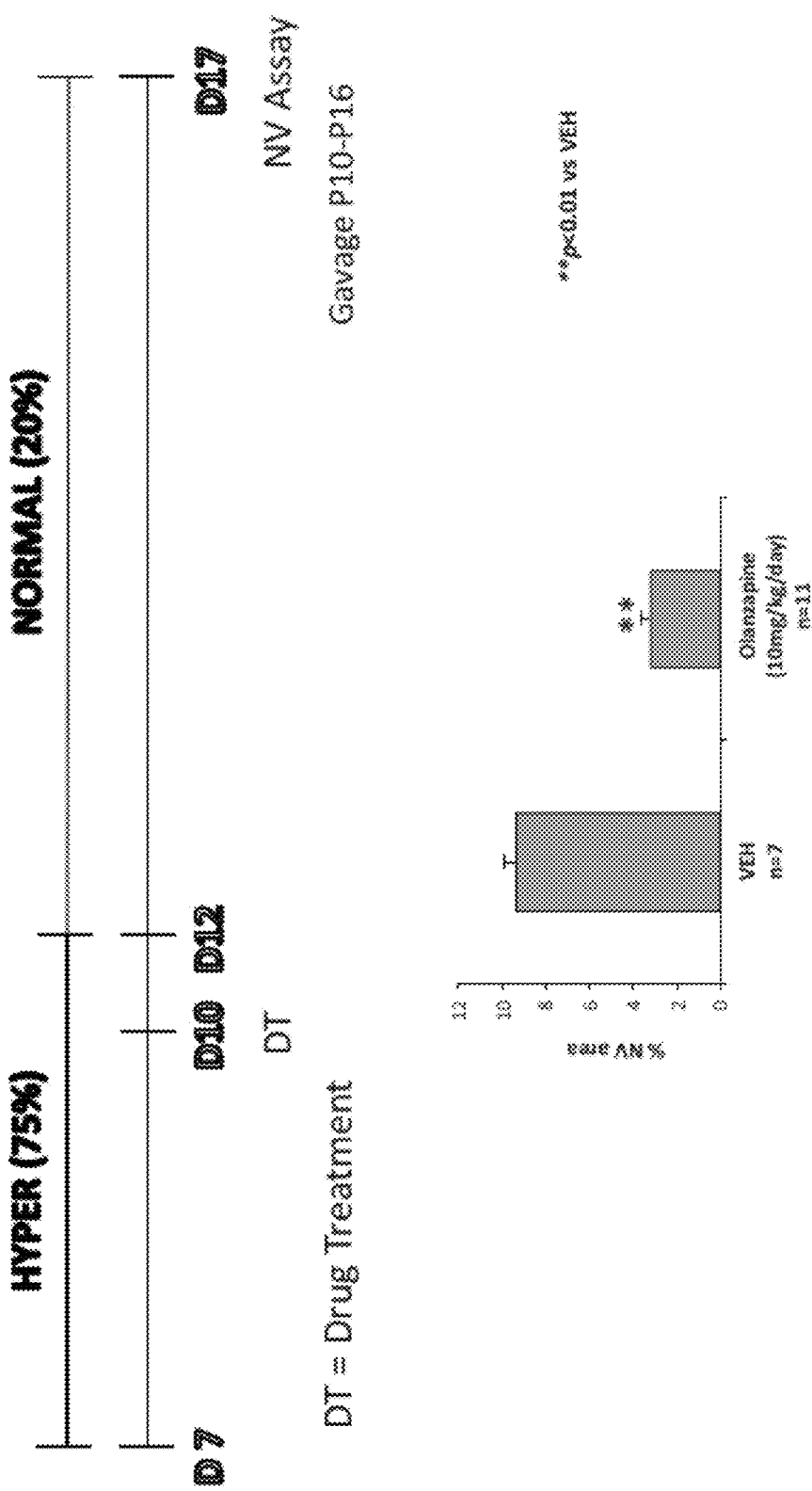
FIG. 10 shows that olanzapine significantly attenuates hyperoxia induced retinal neovascularization. Litters of newborn mice and their dams were placed in a 75% oxygen chamber from P7 to P12. The chamber contained enough food and water for 5 days and was opened only to allow drug administration to the animals. The mice were returned to room air with normal oxygen content on P12. Olanzapine in water or VEH (water) was administered once daily by gavage beginning on P10 and continuing through P16. Retinal neovascularization was evaluated on P17 after 5 days of exposure of the animals to room air. Error bars, SEM.

Retinal angiography and quantification. Retinal neovascularization was evaluated by angiography in mice subjected to OIR as described previously (Smith L E, Wesolowski E, McLellan A, et al. Oxygen-induced retinopathy in the mouse. *Invest Ophthalmol Vis Sci.* 1994;35(1):101-111). P17 mice were deeply anesthetized and then were perfused through the left ventricle with 1 mL of PBS containing 50 mg of high-molecular-weight (2000 kDa) fluorescein-dextran (Sigma, St. Louis, Mo.). Eyes were enucleated and fixed in 4% paraformaldehyde for 24 hours. After removal of the lens, the retina was dissected and wholemounted with glycerol-gelatin. Quantification of retinal neovascularization was performed as described previously (Chen J, Connor K M, Aderman C M, Smith L E. Erythropoietin deficiency decreases vascular stability in mice. *J Clin Invest.* 2008;118(2):526-533). Images of retinal whole-mounts taken at 4× magnification on an epifluorescence microscope (Olympus, Center Valley, Pa.) were imported into Adobe Photoshop 7.0 software (Adobe Systems, Mountain View, Calif.) and merged to produce an image of the entire retina. Neovascularization was quantified as described previously (Bai Y, Ma J X, Guo J, et al. Müller cell-derived VEGF is a significant contributor to retinal neovascularization. *J Pathol.* 2009;219(4):446-454). The Photoshop freehand tool was used to outline areas of neovascular tuft formation, and the area of neovascularization (in pixels) was expressed as a percentage of the area of the whole retina (in pixels). To avoid bias, quantification of neovascularization was performed by an observer masked to the animal treatment. The results are shown in FIG. 10.

Figure 11:
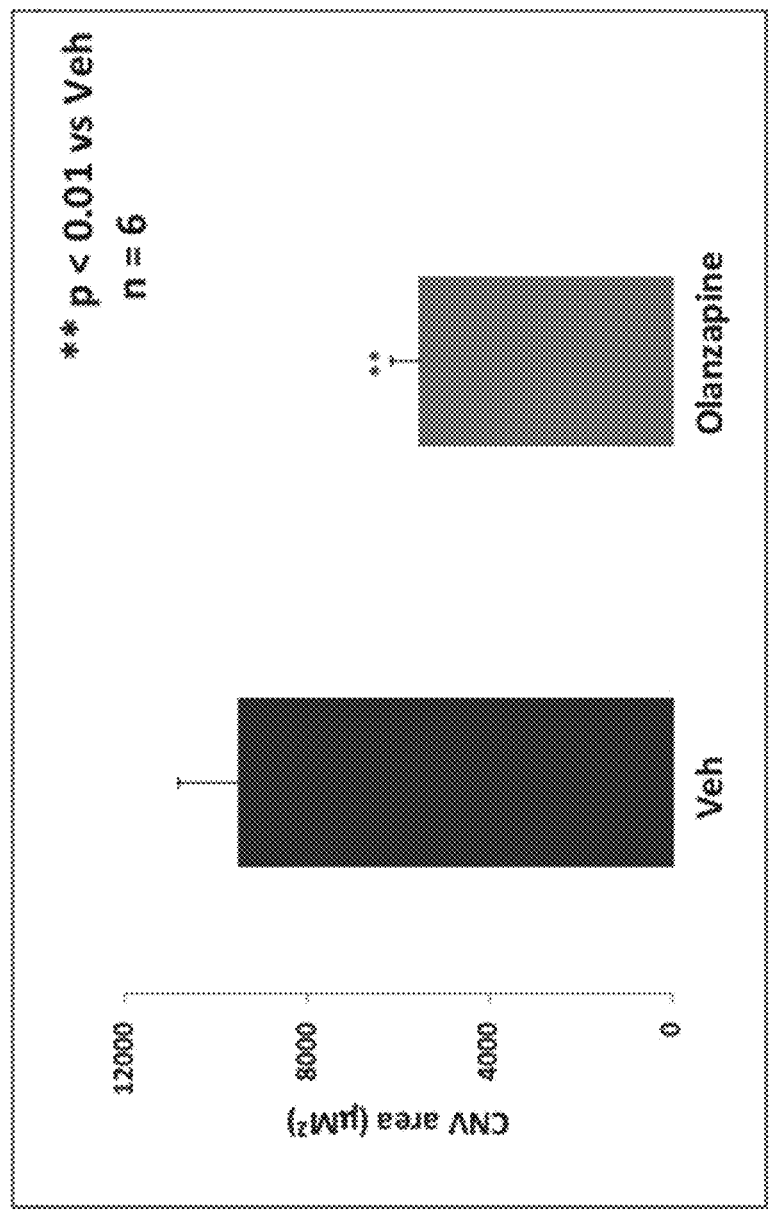
FIG. 11 shows that olanzapine significantly inhibits laser induced choroidal neovascularization in rats. Error bars, SEM.

Choroidal Neovascularization (CNV) Assay: Brown Norway rats (Charles Rivers), weighing 250-300 grams each were used in the study. Drug treatment was started 2 days prior to Laser treatment. Olanzapine was given i.p. (1 mg/kg) once a day for 3 days (day-2, -1 & 0). The last dose on day 0 was delivered about 1 hr before laser treatment. Phosphate buffered saline (PBS) was used for parallel control vehicle IP injection. On day zero of the laser procedure, rat eyes (pupil) were dilated with Tropicamide HCl (1%) and Ak-dilate (10%). Rats were then anesthetized with intramuscular injection of 40 mg/ml Ketamine HCl and 12 mg/ml Xylazine HCL. The fundo's was visualized using a microscope slide coverslip with Refresh Liquigel eye drops as an optical coupling agent. For each animal, 6 laser spots in each eye (360 mW power, 0.07 sec. duration, 50 µm spot size) were made with argon laser (Coherent Inc.; Santa Clara, Calif.) concentrically at approximately equal distances around the optic disc, between every 2 retinal vessels. A single 5-ul volume of the drug (olanzapine) or PBS was injected into the vitreous cavity at day 1, 4 & 6 post-laser photocoagulation procedure. At 11 days after laser treatment, animals were sacrificed by CO2 exposure and CNV formation was assayed as described previously. Briefly, eyes were enucleated and fixed in 10% Formalin solution for 1 hour. Eyes were rinsed in PBS, 5 min×2. or kept in PBS overnight. The eye was thoroughly cleaned and cut in half in a Petri dish leaving the eye cup and attached retina in place. The eye cup-retina was washed in PBS, and retina was separated and removed from the choroid. The eye cup-choroid was incubated overnight in Isolectin $IB_4$ conjugate (10 ug/ml) in PBS/0.5% Triton×100. Eye cup/Choroid was washed in PBS, 20 min×3 and cut in four locations and flat mounted using aqueous mounting media. The area of fluorescence was quantified using Metamorph image analysis software (RPI, Natick, Mass.). The results are shown in FIG. 11.

The experiments establish that the compounds of the invention protect RPEs from oxidative stress (as summarized, below) and the diseases that that such stress causes.

| COMPOUND | PROTECTION (%) AT 10 uM |
| --- | --- |
| Olanzapine | 116 |
| Metabolite A | 103 |
| Metabolite B | 129 |
| Clozapine | 99 |
| n-desmethly clozapine | 77 |

Each and every reference disclosed in the specification, whether non-patent (e.g., scientific, journal references) or patent (granted patents or published patent applications) is incorporated herein by reference in its entirety for all purposes.

The foregoing descriptions details specific methods and compositions that can be employed to practice the present invention, and represents the best mode contemplated. It should not be construed as limiting the overall scope hereof; rather, the ambit of the present invention is to be governed only by the lawful construction of the appended claims.

What is claimed is:

1. A method for treating dry age related macular degeneration, the method comprising administering to a patient in need thereof a compound of the formula

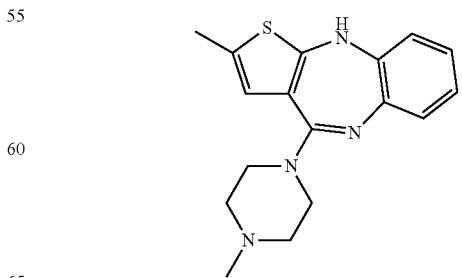

or a pharmaceutically acceptable salt thereof.

2. The method of claim 1, wherein the compound is administered orally.

3. The method of claim 1, wherein the compound is administered by injecting it into the eye.

4. The method of claim 1, wherein the compound is administered topically to the eye.

\* \* \* \* \*